(12) United States Patent
Panton et al.

(10) Patent No.: US 11,850,675 B2
(45) Date of Patent: Dec. 26, 2023

(54) METHOD OF JOINING A SHAPE-MEMORY METAL TO A NON-SHAPE-MEMORY METAL WITH ULTRASONIC ADDITIVE MANUFACTURING

(71) Applicant: Ohio State Innovation Foundation, Columbus, OH (US)

(72) Inventors: Boyd Panton, Columbus, OH (US); Marcelo J. Dapino, Columbus, OH (US); Leon M. Headings, Columbus, OH (US); Mark Bryant Gingerich, Columbus, OH (US); Jennifer L. Morris, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 201 days.

(21) Appl. No.: 17/016,893

(22) Filed: Sep. 10, 2020

(65) Prior Publication Data
US 2021/0069788 A1    Mar. 11, 2021

Related U.S. Application Data

(60) Provisional application No. 62/898,330, filed on Sep. 10, 2019.

(51) Int. Cl.
*B23K 20/10* (2006.01)
*A61M 25/00* (2006.01)
(Continued)

(52) U.S. Cl.
CPC .......... *B23K 20/10* (2013.01); *A61M 25/001* (2013.01); *B22F 1/00* (2013.01); *B22F 10/20* (2021.01);
(Continued)

(58) Field of Classification Search
CPC ................ B23K 20/10; B22F 7/062; A61M 2025/09108; A61M 25/001
See application file for complete search history.

(56) References Cited

U.S. PATENT DOCUMENTS

| 5,211,183 A | * | 5/1993 | Wilson ................. A61M 25/09 |
|---|---|---|---|
| | | | 600/585 |
| 6,450,393 B1 | * | 9/2002 | Doumanidis ......... B29C 64/188 |
| | | | 228/160 |

(Continued)

FOREIGN PATENT DOCUMENTS

| CN | 102501006 B | * | 7/2013 |
|---|---|---|---|
| CN | 106862748 | | 6/2017 |
| JP | 2006204710 A | * | 8/2006 |

OTHER PUBLICATIONS

JP-2006204710-A machine translation (Year: 2006).*
(Continued)

*Primary Examiner* — Michael W Hotchkiss
(74) *Attorney, Agent, or Firm* — Meunier Carlin & Curfman LLC

(57) ABSTRACT

Various implementations include a method of manufacturing one or more devices. The method includes obtaining a base portion of a non-shape-memory metal, disposing one or more shape-memory metal portions along the base portion, and joining at least a first layer of the non-shape-memory metal to the base portion using ultrasonic additive manufacturing. The shape-memory metal portions are disposed along a first base surface of the base portion. The shape-memory metal portions have a first portion contacting the base portion and a second portion spaced apart from the first portion and extending from the base portion. The first layer is joined to the base portion using ultrasonic additive manufacturing and has a first layer surface that is joined to the first base surface. The first layer surface contacts the shape-
(Continued)

memory metal portions when the first layer is joined to the base portion.

70 Claims, 6 Drawing Sheets

(51) Int. Cl.
*B33Y 10/00* (2015.01)
*B22F 10/00* (2021.01)
*B22F 10/20* (2021.01)
*A61M 25/09* (2006.01)
*B33Y 80/00* (2015.01)
*B22F 1/00* (2022.01)

(52) U.S. Cl.
CPC .... *B33Y 10/00* (2014.12); *A61M 2025/09141* (2013.01); *B22F 2999/00* (2013.01); *B33Y 80/00* (2014.12); *F16B 2200/77* (2023.08)

(56) References Cited

U.S. PATENT DOCUMENTS

| | | | |
|---|---|---|---|
| 6,463,349 B2 | 10/2002 | White et al. | |
| 6,519,500 B1 | 2/2003 | White | |
| 7,037,327 B2* | 5/2006 | Salmon | A61F 2/90 623/1.11 |
| 9,101,979 B2* | 8/2015 | Hofmann | C04B 35/64 |
| 10,823,201 B2* | 11/2020 | Kenworthy | F28F 13/12 |
| 2007/0239259 A1* | 10/2007 | Boylan | A61F 2/91 29/6.1 |
| 2007/0295440 A1* | 12/2007 | Stucker | B23K 20/10 156/73.1 |
| 2009/0221898 A1* | 9/2009 | Hillis | A61M 37/0069 600/407 |
| 2015/0044084 A1* | 2/2015 | Hofmann | C21D 1/00 264/642 |
| 2015/0065999 A1* | 3/2015 | Von Segesser | A61B 17/3439 604/523 |
| 2017/0334016 A1* | 11/2017 | Rinker | B23K 20/002 |
| 2018/0311477 A1* | 11/2018 | Telang | A61M 25/09 |
| 2019/0008412 A1* | 1/2019 | Davies | A61B 90/39 |
| 2020/0324362 A1* | 10/2020 | Vogli | C22C 16/00 |

OTHER PUBLICATIONS

Hehr, Interfacial shear strength estimates of NiTieAl matrix composites fabricated via ultrasonic additive manufacturing, Mar. 2015, Elsevier, pp. 200-202 (Year: 2015).*

Kong, Ultrasonic consolidation for embedding SMA fibres within aluminium matrices, Jul. 2004, Elsevier, pp. 421-424 (Year: 2004).*

Koepfer, centerless grinding: not magic!, Dec. 2000, Modern Machine Shop, pp. 1-2 (Year: 2000).*

Friel, Ultrasonic additive manufacturing A hybrid production process for novel functional products, 2013, Elsevier, pp. 35-37 (Year: 2013).*

CN-102501006-B machine translation of the description (Year: 2013).*

"Shape Memory and Superelastic Alloys", Jul. 1999, Copper Development Association, <https://www.copper.org/publications/newsletters/innovations/1999/07/shape.html> (Year: 1999).*

* cited by examiner ns with stainless stee memory metal like Nitinol ("NiTi"). But these devices suffer from being constrained to the physical properties of a single material. Take for example, a pigtail guidewire made entirely of stainless steel, which has a coiled wire at the end for anchoring a catheter. The coiled shape also serves to inhibit the end of the wire from spearing nearby tissue. Because the instrument is entirely made of stainless steel the tip of the instrument may become plastically deformed during insertion through the catheter and may not fully return to the desired coiled shape, introducing a risk that the tip of the wire may spear the patient such as puncturing the walls of heart chambers. If the instrument made entirely of NiTi, the roughly 1 meter long rod that the doctor uses to insert and manipulate the pigtail is difficult to control due to its compliance.

Currently, there are medical instruments that incorporate both a non-shape-memory metal and a shape-memory metal, but these devices use joining methods that severely limit design freedom.

There are a variety of existing technologies that have been developed for joining shape-memory metals, none of which result in a high strength joining process for defect-free shape-memory metal devices. Gluing and soldering create low strength, brittle devices and add mass and size to the devices. Fusion welding techniques, such as micro-resistance welding, damage the material with heat and cause brittle joints due to brittle intermetallics formed by the mixing of alloying elements. Laser welding is widely used because of its low heat input. However, laser welding still forms brittle joints even when using techniques such as interlayers or offsetting the laser to preferentially melt one of the alloys. Rotational friction welding has been used, but the joint geometry is limited, and research in the area shows issues with small process windows. The heat from these current processes can significantly degrade the cyclic shape memory and mechanical properties of the NiTi.

Currently, the most common method for joining actuators is crimping. Issues with crimping include a low pull-out force and significant design input required to achieve reliable joints, with different crimping designs required for different applications.

Thus, there is a need for a method of joining non-shape-memory metal with shape-memory metal to form a device that benefits from the physical properties of both materials while not limiting design freedom or degrading either material.

SUMMARY

Various implementations include a method of manufacturing one or more devices. The method includes obtaining a base portion of a non-shape-memory metal, disposing one or more shape-memory metal portions along the base portion, and joining at least a first layer of the non-shape-memory metal to the base portion using ultrasonic additive manufacturing to form a non-shape-memory metal portion.

The non-shape-memory metal has a first base surface, and the one or more shape-memory metal portions is disposed along the first base surface. The one or more shape-memory metal portions has a first portion and a second portion spaced apart from the first portion. The first portion contacts the base portion and the second portion extends from the base portion. The first layer of the non-shape-memory metal that is joined to the base portion using ultrasonic additive manufacturing has a first layer surface and a second layer surface opposite from the first layer surface that is joined to the first base surface. The second layer surface contacts the one or more shape-memory metal portions when the first layer is joined to the base portion to form the non-shape-memory metal portion.

In some implementations, joining a first layer to the base portion further includes joining one or more additional layers of the non-shape-memory metal to the previously joined layer to form the non-shape-memory portion. Each of the one or more additional layers has a first layer surface and a second layer surface opposite from the first layer surface of the additional layer. The second layer surface of the additional layer is joined to the first layer surface of the previously joined layer.

In some implementations, after obtaining a base portion, the method further includes forming one or more grooves in the first base surface. The first portion of one or more of the shape-memory metal portions are disposed within the one or more grooves.

In some implementations, obtaining a base portion includes joining one or more base layers of the non-shape-memory metal to each other using ultrasonic additive manufacturing. Each of the one or more base layers has a first base layer surface and a second base layer surface opposite from the first base layer surface. The first base layer surfaces and second base layer surfaces of adjacent base layers are joined to each other.

In some implementations, obtaining a base portion includes joining one or more base layers of the non-shape-memory metal to the base portion using ultrasonic additive manufacturing to form the first base surface.

In some implementations, obtaining a base portion includes machining the base portion to flatten the first base surface.

In some implementations, the non-shape-memory metal includes a steel alloy, a titanium alloy, an aluminum alloy, or a copper alloy.

In some implementations, the non-shape-memory metal includes a medical grade metal. In some implementations, the medical grade metal includes stainless steel.

In some implementations, the shape-memory metal includes a medical grade metal. In some implementations, the medical grade metal includes NiTi. In some implementations, the shape-memory metal includes a Cu-based alloy or a Fe-based alloy.

In some implementations, the one or more shape-memory metal portions are medical instrument tips and the one or more devices manufactured by the method is a medical instrument.

In some implementations, the one or more devices manufactured by the method is a medical implant.

In some implementations, after joining the first layer to the base portion, the method further includes machining the non-shape-memory metal portion. In some implementations, the non-shape-memory metal portion is machined using centerless grinding. In some implementations, the one or more shape-memory metal portions is two or more shape-memory metal portions. The non-shape-memory metal portion is machined to form two or more separate devices. Each of the devices includes at least one of the two or more shape-memory metal portions.

In some implementations, before joining the first layer to the base portion, the method further includes disposing a radiopaque material along the first base surface. The second layer surface contacts the radiopaque material when the second layer is joined to the base portion.

In some implementations, after joining the first layer to the base portion, the method further includes welding the non-shape-memory metal portion to another device that includes the non-shape-memory metal or a different non-shape-memory metal. In some implementations, after joining the first layer to the base portion, the method further includes welding the shape-memory metal portion to another device that includes the shape-memory metal or a different shape-memory metal.

BRIEF DESCRIPTION OF DRAWINGS

Example features and implementations are disclosed in the accompanying drawings. However, the present disclosure is not limited to the precise arrangements and instrumentalities shown.

DETAILED DESCRIPTION

Figure 1:
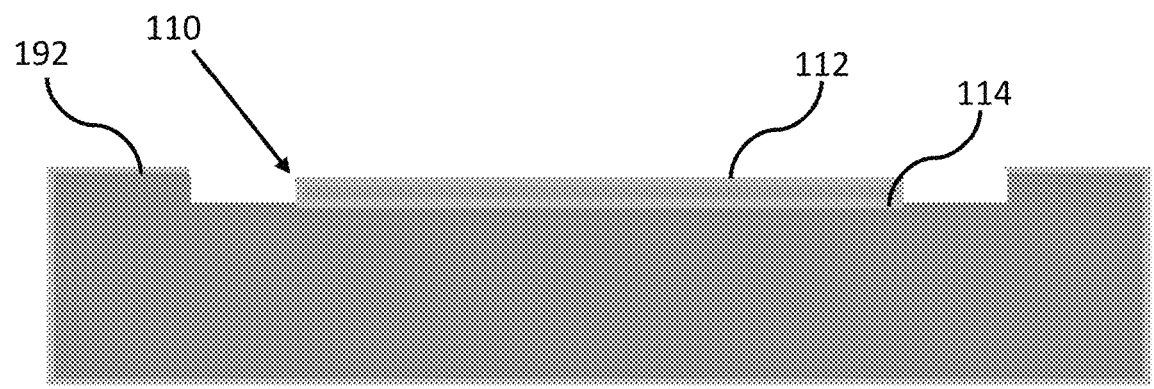
FIG. 1 is a front view of a build plate of a UAM machine with a single base layer on the build plate, according to one implementation.

The devices, systems, and methods disclosed herein provide for the joining of a shape-memory metal to a non-shape-memory material using ultrasonic additive manufacturing ("UAM"). More specifically, some implementations disclose a method of surgical instruments fabrication by UAM that consist of both stainless steel alloys and a shape-memory alloy such as, but not exclusive to, Nitinol ("NiTi"). Shape-memory metal is embedded within the non-shape-memory metal portion using UAM and extends out of the non-shape-memory metal, providing a strong, gapless joint between the materials. Parts are built up by welding layers of a medical grade non-shape-memory metal such as stainless steel 316 or 304. During the build process, a shape-memory metal, such as NiTi wire or ribbon, is placed between layers of the non-shape-memory metal, with or without the use of a channel. The build process continues until the part is larger than the desired dimensions. This part is then machined to the instrument's final dimensions. For example, the instrument may be machined using centerless grinding to produce a small diameter (e.g., 0.030 inches [0.0762 mm]) rod with a NiTi wire protruding out of the end of a stainless steel rod. The NiTi may pass through the entire length of the surgical instrument or terminate within a shorter length of stainless steel. In the latter case, the end without NiTi may be welded using conventional welding techniques to another piece of stainless steel rod to provide the required total instrument length.

The advantage of the disclosed devices, systems, and methods over state-of-the-art instruments is that UAM enables the best features of both stainless steel (or other non-shape-memory metal) and NiTi (or other shape-memory metal) in the same instrument. Incorporating both NiTi and stainless steel allows for the shape retention and high strain recovery of NiTi for tools at the end of the instrument, while providing the stiffness of stainless steel for the rest of the instrument, which provides a doctor or other user of the device better control of the device. The methods disclosed herein also provide devices that exhibit other shape-memory properties, such as, but not limited to, pseudoelasticity and solid-state phase transformation. The solid-state phase transformation property of shape-memory metals causes the shape-memory metal to bend as the shape-memory metal reacts to changes in temperature (e.g., the temperature differential between room temperature and the core temperature of user's body). This bending effect can be used for actuation and sensing applications in devices.

As discussed above, the heat from a fusion process like welding significantly degrades the mechanical properties of NiTi. In contrast, UAM is a solid-state welding process that enables embedding NiTi in stainless steel at temperatures well below the melting points of the metals used, retaining the mechanical and smart properties of NiTi without the formation of brittle intermetallics. Evidence of metallurgical bonding between UAM joined Al and NiTi foils has been found, so metallurgical bonding between stainless steel and NiTi wires is achievable. However, even without a metallurgical bond, UAM may achieve an adequate joint strength through a friction fit from mechanical encapsulation of the NiTi within the stainless steel. UAM produces intimate contact between the materials at the scale of the materials' asperities, providing a gapless interface.

Industrial applications for the disclosed devices, systems, and methods include, but are not limited to, medical grade instruments such as grasping forceps, pigtail and other surgical guidewires, hingeless instruments, and dissecting spatulas. The disclosed devices, systems, and methods may also be applied to other medical applications in the optometry and dentistry fields.

Various implementations include a method of manufacturing one or more devices. The method includes obtaining a base portion of a non-shape-memory metal, disposing one or more shape-memory metal portions along the base portion, and joining at least a first layer of the non-shape-memory metal to the base portion using ultrasonic additive manufacturing to form a non-shape-memory metal portion.

The non-shape-memory metal has a first base surface, and the one or more shape-memory metal portions is disposed along the first base surface. The one or more shape-memory metal portions has a first portion and a second portion spaced apart from the first portion. The first portion contacts the base portion and the second portion extends from the base portion. The first layer of the non-shape-memory metal that is joined to the base portion using ultrasonic additive manufacturing has a first layer surface and a second layer surface opposite from the first layer surface that is joined to the first base surface. The second layer surface contacts the one or more shape-memory metal portions when the first layer is joined to the base portion to form the non-shape-memory metal portion.

FIGS. 1-11B show a method of manufacturing a device by joining stainless steel and Nitinol ("NiTi") using ultrasonic additive manufacturing ("UAM").

FIG. 1 shows a build plate 192 of a UAM machine 190. A base layer 110 of non-shape-memory metal is disposed on the build plate 192. The base layer 110 of non-shape-memory metal has a first base layer surface 112 and a second base layer surface 114 opposite from the first base layer surface 112. The second base layer surface 114 is disposed on the build plate 192.

Figure 2:
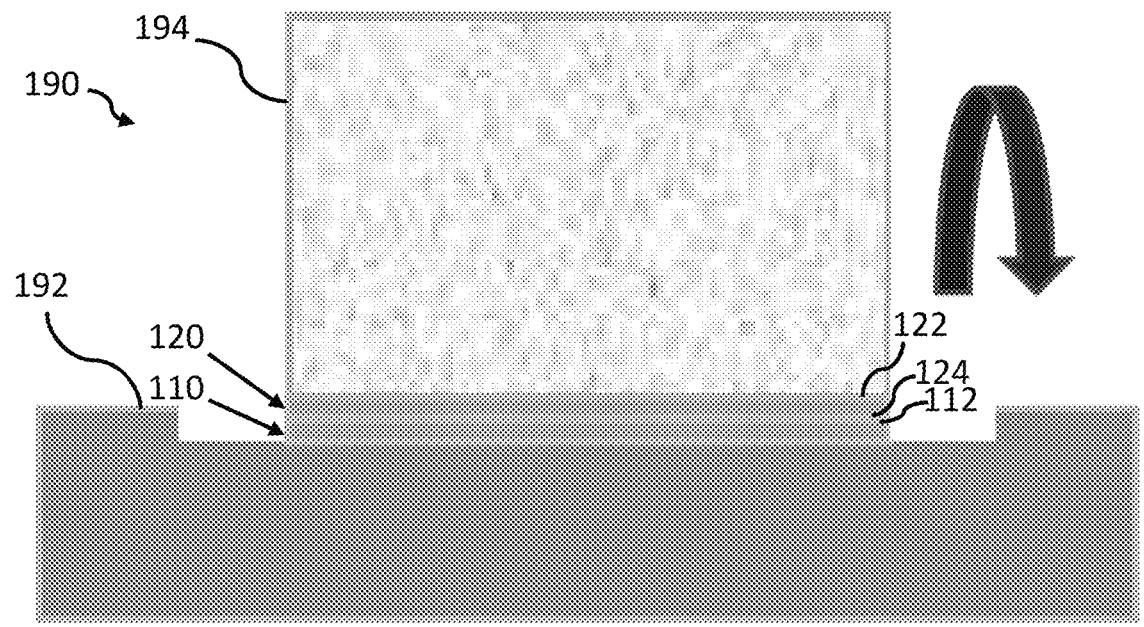
FIG. 2 is a front view of the build plate of FIG. 1 showing a subsequent base layer being joined to the single base layer through UAM.

FIG. 2 shows a subsequent base layer 120 being joined to the previous base layer 110. Like the previous base layer 110, the subsequent base layer 120 of non-shape-memory metal has a first base layer surface 122 and a second base layer surface 124 opposite from its first base layer surface 122. The second base layer surface 124 of the subsequent base layer 120 is disposed on the first base layer surface 112 of the previous base layer 110.

The UAM machine 190 includes a welding horn 194 that applies pressure to the layers 110, 120 through a normal force and generates ultrasonic motion that causes the layers 110, 120 to bond. The welding horn 194 is extended toward the first surface 122 of the subsequent base layer 120 such that the welding horn 194 exerts enough pressure and ultrasonic vibration to the previous and subsequent base layers 110, 120 to cause the layers 110, 120 to bond to each other.

Figure 3:
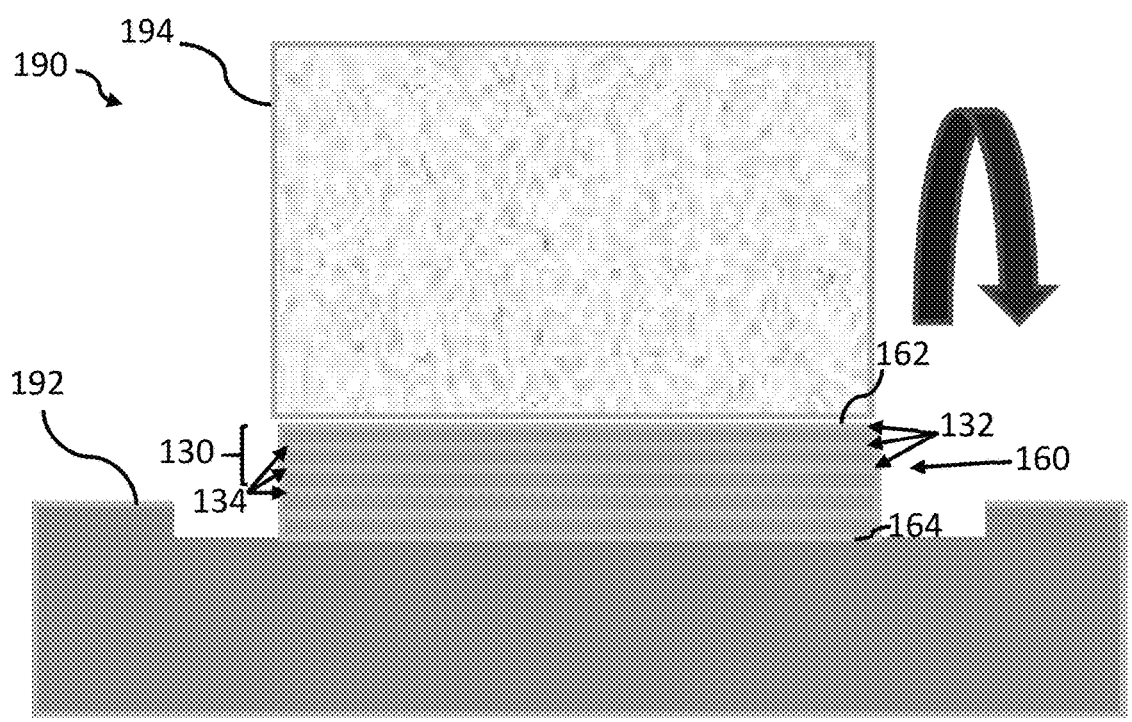
FIG. 3 is a front view of the build plate of FIG. 1 showing base layers being joined to the subsequent base layer and the single base layer through UAM to form a base portion.

FIG. 3 shows three more base layers 130 of non-shape-memory metal joined to the previously joined base layers 110, 120. As with the previously joined base layers 110, 120, each of the three more base layers 130 has a first base layer surface 132 and a second base layer surface 134 opposite from its first base layer surface 132. The second base layer surface 134 of one base layer is disposed on the first base layer surface 122, 132 of the previously joined base layer. The welding horn 194 is then pressed against that base layer and ultrasonic vibrations are generated to join the second base layer surface 134 of that base layer to the first base layer surface 122, 132 of the previously joined base layer. This joining process is repeated for each base layer 130 to form a base portion 160. The first base layer surface 132 of the last joined base layer defines the first base surface 162 of the base portion 160, which is opposite and spaced apart from the second base surface 164.

Figure 4:
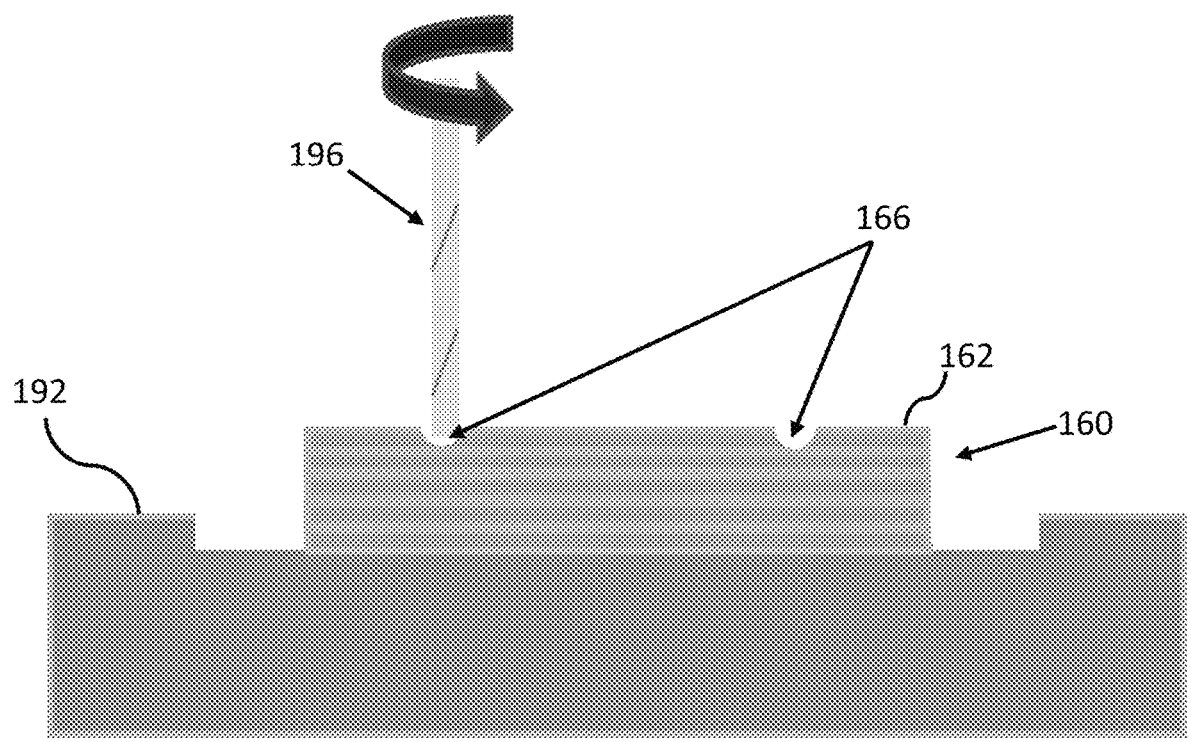
FIG. 4 is a front view of the build plate of FIG. 1 showing an endmill forming grooves in the base portion.
Figure 5:
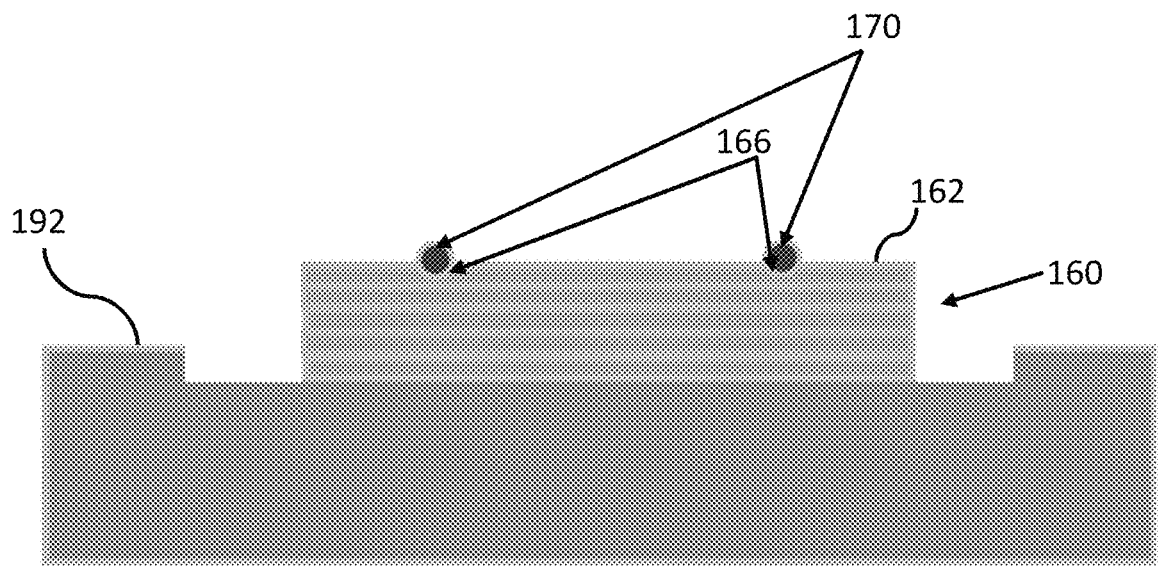
FIG. 5 is a front view of the build plate of FIG. 1 showing two shape-memory metal portions being disposed within the grooves of the base portion.
Figure 6:
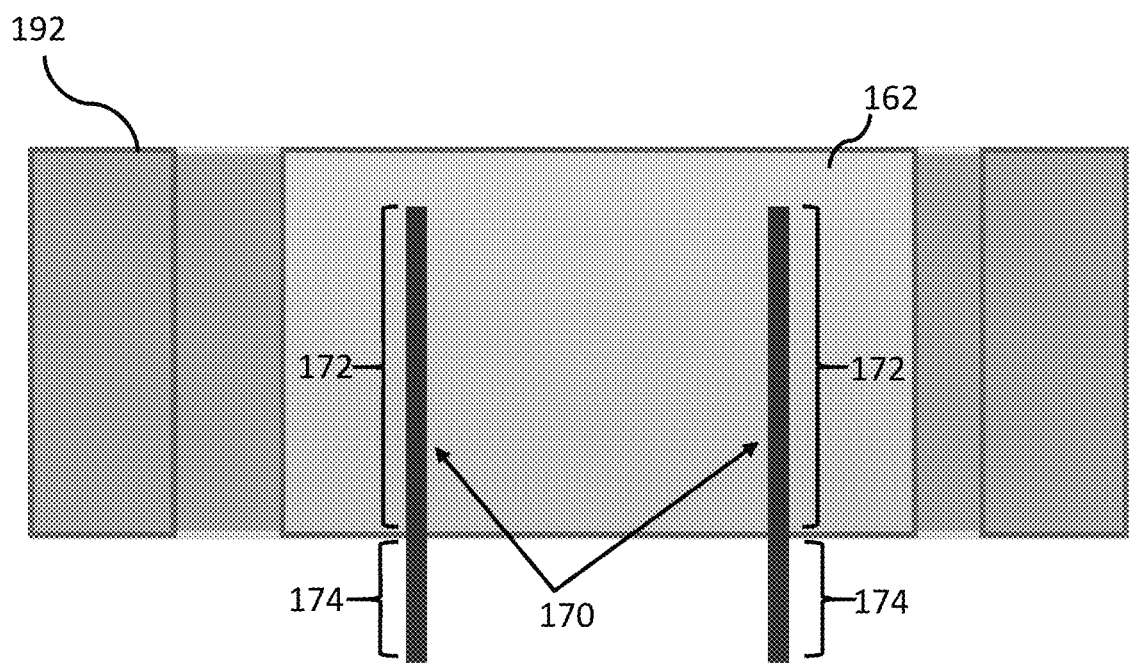
FIG. 6 is a top view of FIG. 5. showing two shape-memory metal portions being disposed within the grooves of the base portion.

FIG. 4 shows an endmill 196 machining the first base surface 162 to form two grooves 166 along the first base surface 162. FIG. 5 shows two shape-memory metal portions 170 disposed within the grooves 166 defined by the first base surface 162. As seen in FIG. 6, each of the shape-memory metal portions 170 has a first portion 172 and a second portion 174 spaced apart from the first portion 172. The first portion 172 of the shape-memory metal portion 170 is disposed within the groove 166 such that it contacts the base portion 160. The second portion 174 of the shape-memory metal portion 170 extends from the base portion 160.

Figure 7:
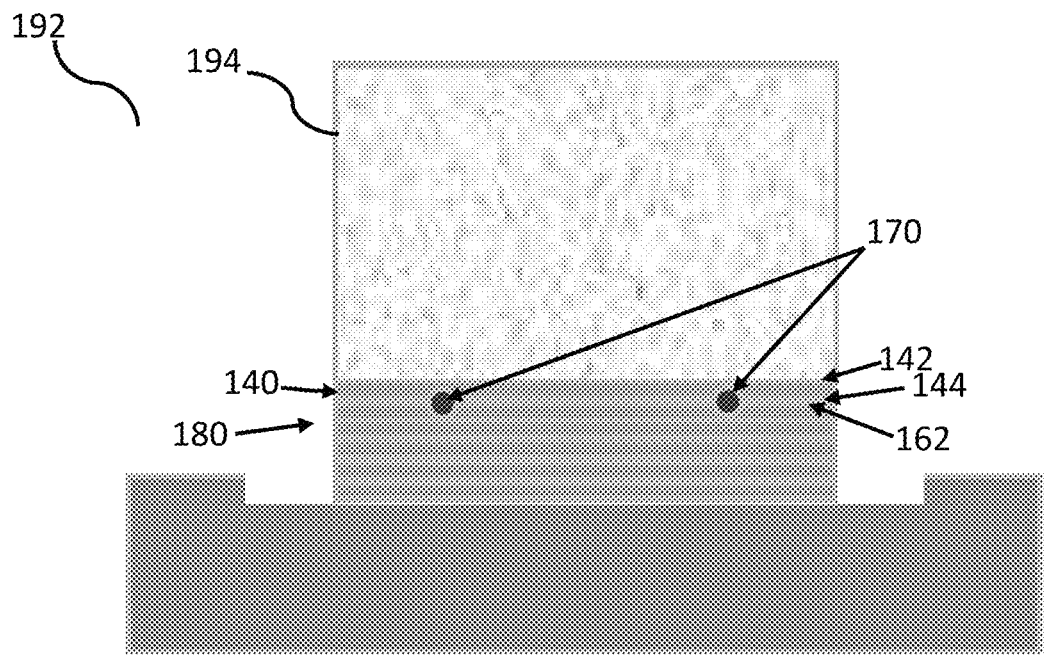
FIG. 7 is a front view of the build plate of FIG. 1 showing a first layer being joined to the base portion through UAM to form a non-shape-memory metal portion.

FIG. 7 shows a first layer 140 of the same non-shape-memory metal as the base layers 110, 120, 130 being joined to the base portion 160 using UAM. The first layer 140 has a first layer surface 142 and a second layer surface 144 opposite from the first layer surface 140. The second layer surface 144 is disposed on the first base surface 162. Because the first portions 172 of the shape-memory metal portions 170 extend partially out of their respective grooves 166, the second layer surface 144 contacts the one or more shape-memory metal portions 170. The first layer 140 is joined to the first base surface 162 using UAM. The joined first layer 140 and base portion 160 form a non-shape-memory metal portion 180. Because the welding horn 194 applies pressure to the first layer 140 as the first layer 140 is joined to the first base surface 162, the shape-memory metal portions 170 that are extending partially out of the grooves 166 are embedded in the non-shape-memory metal portion 180 by a strong pressure fit.

Figure 8:
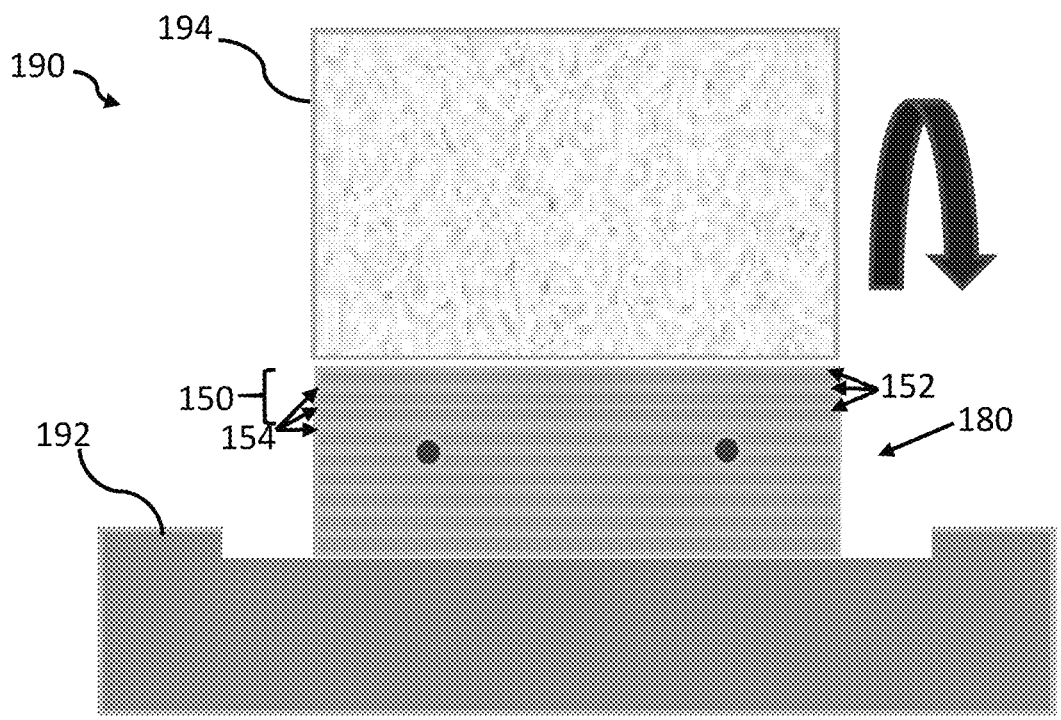
FIG. 8 is a front view of the build plate of FIG. 1 showing additional layers being joined to the non-shape-memory metal portion through UAM.

FIG. 8 shows three additional layers 150 of non-shape-memory metal being joined to the non-shape-memory metal portion 180 using UAM. The second layer surface 154 of each of the additional layers 150 is joined to the first layer surface 142, 152 of the previously joined layer. The first layer surface 152 of the last joined additional layer defines the top surface 182 of the non-shape-memory metal portion 180, which is opposite and spaced apart from the bottom surface 184 of the non-shape-memory metal portion 180.

Although FIGS. 1-3 show a total of five base layers 110, 120, 130 being layered and joined to each other and FIGS. 7 and 8 show a total of four additional layers 140, 150 being layered and joined to the base layers 110, 120, 130, in other implementations, any number of base layers and additional layers are joined to each other to form a desired thickness of the non-shape-memory metal portion. The base layers 110, 120, 130 and additional layers 140, 150 of non-shape memory metal shown in FIGS. 1-8 are stainless steel tape, but in other implementations, the non-shape memory metal is any other non-shape-memory metal capable of joining two pieces of the non-shape-memory metal together using UAM. In some implementations, the non-shape-memory metal includes any steel alloy, a titanium alloy, an aluminum alloy, a copper alloy, a nickel alloy, a refractory alloy, or a radiopaque alloy. In some implementations, the non-shape-memory metal includes any medical grade metal.

Although FIGS. 5-8 show two shape-memory metal portions 170 being joined to the non-shape-memory metal portion 180, in other implementations, any number of shape-memory metal portions are disposed between the first base surface and the first layer to join the shape-memory metal portions to the non-shape-memory metal portion. FIGS. 4-6 show two grooves 166 formed along the first base surface 162 with two shape-memory metal portions 170 disposed within the grooves 166, but in other implementations, any number of grooves are formed in the first base surface to accommodate a desired number of shape-memory metal portions. In some implementations, no grooves are formed in the first base surface and the shape-memory metal portions are disposed on the first base surface. In some implementations, two or more shape-memory metal portions are disposed within the same groove. The grooves 166 formed in the first base surface 162 in FIG. 4 extend along straight, parallel lines, but in other implementations, the grooves are any shape and are not parallel to each other. In some implementations, the grooves are formed such that the shape-memory metal portions disposed within the individual grooves extend from different surfaces of the non-shape-memory metal portion.

In some implementations, other materials, such as a radiopaque material, are disposed on the first base surface or in grooves formed in the first base surface and are joined to the non-shape-memory metal portion similar to the shape-memory metal portions.

As used herein, the term "shape-memory metal" includes any metal that exhibits shape-memory properties and/or superelastic properties.

The shape memory metal portions 170 shown in FIGS. 5-8 are Nitinol ("NiTi") wire, but in other implementations, the shape-memory metal portions are any shape-memory metal. In some implementations, two or more shape-memory metal portions embedded in the same non-shape-memory metal portion can be different shape-memory metals. In some implementations, the shape-memory metal portions include Ti—Ni—Pd, Ti—Ni—Pt, Ni—Ti—Hf, Ni—Ti—Zr, Cu—Al—Ni, Cu—Al—Nb, Co—Al, Co—Ni—Al, Ni—Al, Ni—Mn, Ni—Mn—Ga, Zr—Cu, Ti—Nb, U—Nb, Ti—Pd, Ti—Au, Ti—Pt—Ir, Ta—Ru, Nb—Ru, Ni—Ti—Hf—Zr, Ni—Ti—Er, and/or any shape-memory alloy. In some implementations, the shape-memory metal portions include any NiTi-based, Cu-based, and/or Fe-based alloys. In some implementations, the shape-memory metal portions include a medical grade metal.

Figure 9:
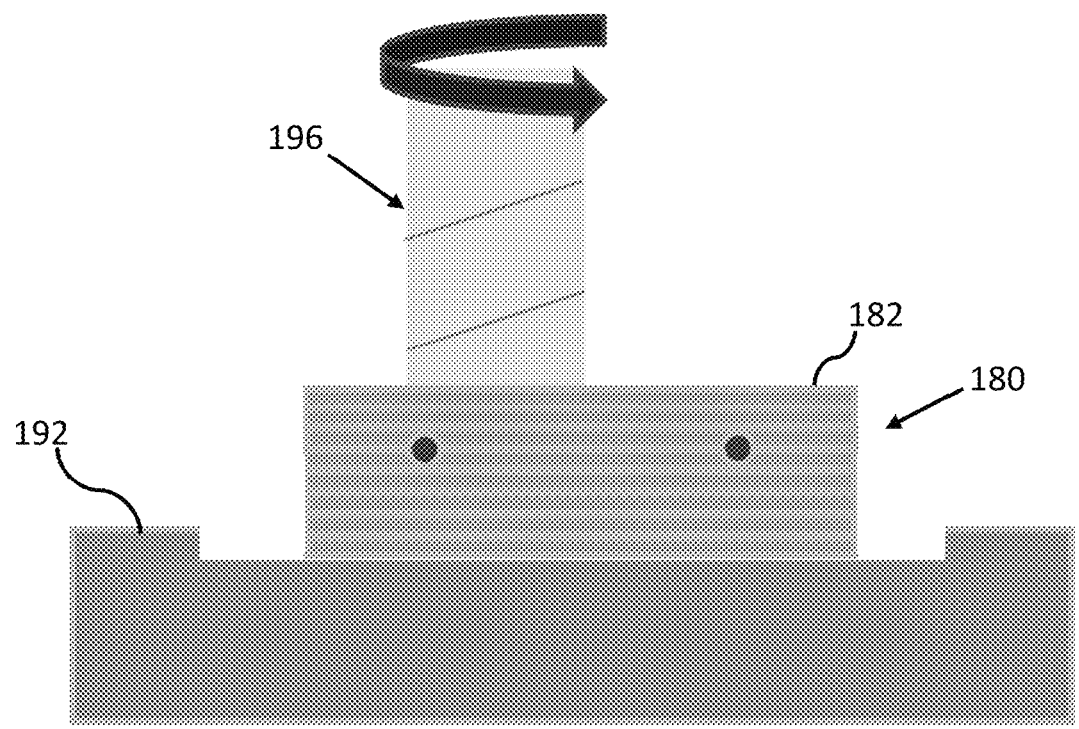
FIG. 9 is a front view of the build plate of FIG. 1 showing the endmill machining the top surface of the non-shape-memory metal portion.

FIG. 9 shows the endmill 196 machining the non-shape-memory metal portion 180 to flatten the top surface 182 of the non-shape-memory metal portion 180. Because the first portions 172 of the shape-memory metal portions 170 partially extend from the grooves 166, the shape-memory metal portions 170 cause the additional layers 140, 150 of non-shape-memory metal that are joined to the base portion 160 to bow slightly around the shape-memory metal portions 170. The bow in the additional layers 140, 150 of non-shape-memory metal can be removed by machining the top surface 182 of the non-shape-memory metal portion 180 flat.

Figure 10:
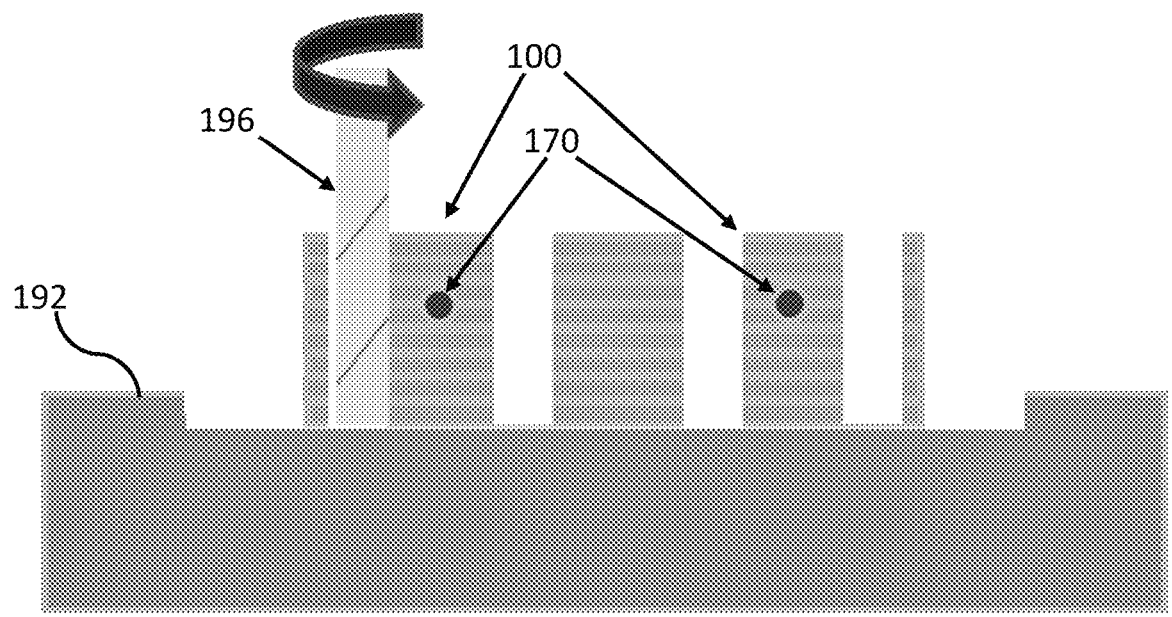
FIG. 10 is a front view of the build plate of FIG. 1 showing the endmill separating the non-shape-memory metal portion into multiple devices.

FIG. 10 shows the endmill 196 further machining the non-shape-memory metal portion 180 into separate devices 100 by severing each of the base layers 110, 120, 130 and additional layers 140, 150 of the non-shape-memory metal portion 180. Each of the devices 100 shown in FIGS. 10-11B includes one of the shape-memory metal portions 170, but in other implementations, each device can include two or more shape-memory metal portions.

Figure 11A:
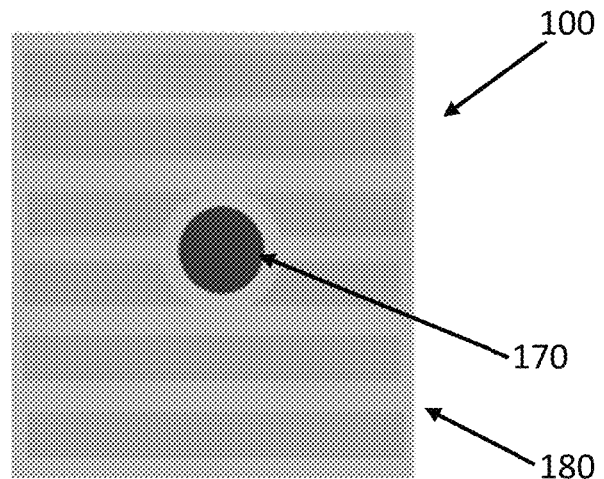
FIG. 11A is a front view of a single device as shown in FIG. 10.
Figure 11B:
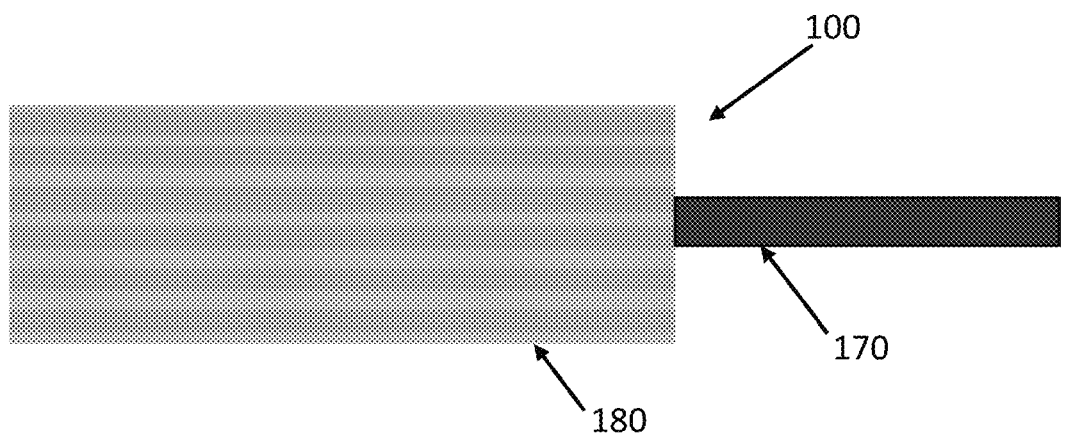
FIG. 11B is a side view of the device of FIG. 11A.

The separate devices 100 can then be further machined into any desired shape, as shown in FIGS. 11A and 11B. As seen in FIGS. 11A and 11B, the non-shape-memory metal portion 170 of the device 100 is machined into a rectangular prism, however in other implementations, the non-shape-memory metal portion is machined to form any other three-dimensional shape. In some implementations, the non-shape-memory metal portion is machined into a cylinder by using centerless grinding, for example. In some implementations, the non-shape-memory metal portion is coupled to another device by welding, one or more fastener, or any other way of joining a non-shape-memory metal to another material.

The method shown in FIGS. 1-11B includes a base portion and additional layers made of non-shape-memory metal and shape-memory metal portions embedded in the non-shape-memory metal. However, in some implementations, the metals can be switch such that the method includes a base portion and additional layers made of a shape-memory metal and non-shape-memory metal portions embedded in the shape-memory metal.

The cross-sectional shape of the shape-memory metal portions 170 as viewed in a plane perpendicular to a longitudinal axis of the shape-memory metal portions 170 are circular in FIG. 11A, but in other implementations, the cross-sectional shape of the shape-memory metal portions is a flat sheet, a triangle, any quadrilateral, a pentagon, a hexagon, or any other shape. A cross-sectional shape of the grooves can correspond to the cross-sectional shape of the shape-memory metal portion or can be any other shape. In some implementations, the first and second portions of the shape-memory metal portion have different cross-sectional shapes. In some implementations, the cross-sectional shape of the shape-memory metal portions change along the longitudinal axis.

The shape-memory metal portion 170 shown in FIG. 11A has a width of 0.010 inches as measured across its cross-section. However, in other implementations, the width of the shape-memory metal portion is any width, such as 0.017 inches. The length of the second portion of the shape-memory metal portion 170 shown in FIG. 11B, as measured from the non-shape-memory metal portion to the tip of the second portion, is 6 inches long, but in other implementations, the length of the shape-memory metal portion is any length.

Although the second portion 174 of the shape-memory metal 170 portion shown in FIGS. 11A and 11B extends along a straight line, in other implementations, the shape-memory metal portion contains any number of bends or curves to form any desired shape. In some implementations, the tip of the second portion can be embedded in the non-shape-memory metal portion of the same or a different device using the UAM methods described herein.

The device manufactured by the methods disclosed herein could be used as a coupler for coupling other non-shape-memory metal devices to other shape-memory metal devices. After the devices are completed, the non-shape-memory metal portion of the device can be welded to the same or different non-shape-memory metal in a separate device. Similarly, the shape-memory metal portion(s) of the device can be welded to the same or different shape-memory metal in a separate device.

In some implementations, the shape-memory metal portion is a medical instrument tip and the device is a medical instrument. In some implementations, the device is a medical implant. In some implementations, the device is designed for an aerospace, automotive, robotics, civil structure, piping, telecommunications, or and other application which can benefit from hybrid active-passive metal parts. In some implementations, the device(s) manufactured by the methods disclosed herein include, but are not limited to, an actuation device, a sensing device, a compliant device, a locking device, or a micro-electro-mechanical device. For example, by offsetting an embedded NiTi wire from the center of the non-shape-memory metal, the solid-state phase transformation property of shape-memory metal can cause actuation of the NiTi, which could cause bending of the host structure. This may be used for applications such as robot actuators, active valves, and orthodontics. When centered, actuation/deactivation of the NiTi may serve to vary the stiffness of the hybrid structure to regulate force transmitted forces or tune vibrational response. Embedded NiTi can also provide structural damping.

A number of implementations have been described. Nevertheless, it will be understood that various modifications may be made without departing from the spirit and scope of the claims. Accordingly, other implementations are within the scope of the following claims.

Certain terminology is used herein for convenience only and is not to be taken as a limitation on the present claims. In the drawings, the same reference numbers are employed for designating the same elements throughout the several figures. A number of examples are provided, nevertheless, it will be understood that various modifications can be made without departing from the spirit and scope of the disclosure herein. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. Although the terms "comprising" and "including" have been used herein to describe various implementations, the terms "consisting essentially of" and "consisting of" can be used in place of "comprising" and "including" to provide for more specific implementations and are also disclosed.

What is claimed is:

1. A method of manufacturing one or more devices, the method comprising: obtaining a base portion of a non-shape-memory metal, the non-shape-memory metal having a first base surface; disposing one or more shape-memory metal portions along the first base surface, the one or more shape-memory metal portions having a longitudinal axis, a first portion, and a second portion axially spaced apart from the first portion along the longitudinal axis, wherein the first portion contacts the base portion and the second portion extends from the base portion; joining a first layer of the non-shape-memory metal to the base portion using ultrasonic additive manufacturing to form a non-shape-memory portion, the first layer having a first layer surface and a second layer surface opposite from the first layer surface that is joined to the first base surface, wherein the second layer surface contacts the one or more shape-memory metal portions; and welding the non-shape-memory metal portion to another device that includes the non-shape-memory metal or a different non-shape-memory metal, wherein the one or more devices is a medical implant.

2. The method of claim 1, wherein joining a first layer to the base portion further includes joining one or more additional layers of the non-shape-memory metal to the previously joined layer to form the non-shape-memory portion, each of the one or more additional layers having a first layer surface and a second layer surface opposite from the first layer surface of the additional layer, the second layer surface of the additional layer being joined to the first layer surface of the previously joined layer.

3. The method of claim 1, wherein, after obtaining a base portion, the method further comprises forming one or more grooves in the first base surface, wherein the first portion of one or more of the shape-memory metal portions are disposed within the one or more grooves.

4. The method of claim 1, wherein obtaining a base portion includes joining one or more base layers of the non-shape-memory metal to each other using ultrasonic additive manufacturing, each of the one or more base layers having a first base layer surface and a second base layer surface opposite from the first base layer surface, wherein the first base layer surfaces and second base layer surfaces of adjacent base layers are joined to each other.

5. The method of claim 1, wherein obtaining a base portion includes joining one or more base layers of the non-shape-memory metal to the base portion using ultrasonic additive manufacturing to form the first base surface.

6. The method of claim 1, wherein obtaining a base portion includes machining the base portion to flatten the first base surface.

7. The method of claim 1, wherein the non-shape-memory metal includes a steel alloy, a titanium alloy, an aluminum alloy, or a copper alloy.

8. The method of claim 1, wherein the shape-memory metal includes a Cu-based alloy or a Fe-based alloy.

9. The method of claim 1, wherein before joining the first layer to the base portion, the method further comprises disposing a radiopaque material along the first base surface, wherein the second layer surface contacts the radiopaque material when the second layer is joined to the base portion.

10. The method of claim 1, wherein after joining the first layer to the base portion, the method further comprises welding the shape-memory metal portion to another device that includes the shape-memory metal or a different shape-memory metal.

11. The method of claim 1, wherein the non-shape-memory metal includes a medical grade metal.

12. The method of claim 11, wherein the medical grade metal includes stainless steel.

13. The method of claim 1, wherein the shape-memory metal includes a medical grade metal.

14. The method of claim 13, wherein the medical grade metal includes NiTi.

15. The method of claim 1, wherein, after joining the first layer to the base portion, the method further comprises machining the non-shape-memory metal portion.

16. The method of claim 15, wherein the non-shape-memory metal portion is machined using centerless grinding.

17. The method of claim 15, wherein the one or more shape-memory metal portions is two or more shape-memory metal portions, wherein the non-shape-memory metal portion is machined to form two or more separate devices, each of the devices including at least one of the two or more shape-memory metal portions.

18. A method of manufacturing one or more devices, the method comprising:
    obtaining a base portion of a non-shape-memory metal, the non-shape-memory metal having a first base surface;
    disposing one or more shape-memory metal portions along the first base surface, the one or more shape-memory metal portions having a longitudinal axis, a first portion, and a second portion axially spaced apart from the first portion along the longitudinal axis, wherein the first portion contacts the base portion and the second portion extends from the base portion;
    joining a first layer of the non-shape-memory metal to the base portion using ultrasonic additive manufacturing to form a non-shape-memory portion, the first layer having a first layer surface and a second layer surface opposite from the first layer surface that is joined to the first base surface, wherein the second layer surface contacts the one or more shape-memory metal portions;
    after joining the first layer to the base portion, machining the non-shape-memory metal portion using centerless grinding, and
    welding the non-shape-memory metal portion to another device that includes the non-shape-memory metal or a different non-shape-memory metal.

19. The method of claim 18, wherein joining a first layer to the base portion further includes joining one or more additional layers of the non-shape-memory metal to the previously joined layer to form the non-shape-memory portion, each of the one or more additional layers having a first layer surface and a second layer surface opposite from the first layer surface of the additional layer, the second layer surface of the additional layer being joined to the first layer surface of the previously joined layer.

20. The method of claim 18, wherein, after obtaining a base portion, the method further comprises forming one or more grooves in the first base surface, wherein the first portion of one or more of the shape-memory metal portions are disposed within the one or more grooves.

21. The method of claim 18, wherein obtaining a base portion includes joining one or more base layers of the non-shape-memory metal to each other using ultrasonic additive manufacturing, each of the one or more base layers having a first base layer surface and a second base layer surface opposite from the first base layer surface, wherein the first base layer surfaces and second base layer surfaces of adjacent base layers are joined to each other.

22. The method of claim 18, wherein obtaining a base portion includes joining one or more base layers of the non-shape-memory metal to the base portion using ultrasonic additive manufacturing to form the first base surface.

23. The method of claim 18, wherein obtaining a base portion includes machining the base portion to flatten the first base surface.

24. The method of claim 18, wherein the non-shape-memory metal includes a steel alloy, a titanium alloy, an aluminum alloy, or a copper alloy.

25. The method of claim 18, wherein the shape-memory metal includes a Cu-based alloy or a Fe-based alloy.

26. The method of claim 18, wherein the one or more shape-memory metal portions are medical instrument tips and the one or more devices manufactured by the method is a medical instrument.

27. The method of claim 18, wherein the one or more devices manufactured by the method is a medical implant.

28. The method of claim 18, wherein the one or more shape-memory metal portions is two or more shape-memory metal portions, wherein the non-shape-memory metal portion is machined to form two or more separate devices, each of the devices including at least one of the two or more shape-memory metal portions.

29. The method of claim 18, wherein before joining the first layer to the base portion, the method further comprises disposing a radiopaque material along the first base surface, wherein the second layer surface contacts the radiopaque material when the second layer is joined to the base portion.

30. The method of claim 18, wherein after joining the first layer to the base portion, the method further comprises welding the shape-memory metal portion to another device that includes the shape-memory metal or a different shape-memory metal.

31. The method of claim 18, wherein the non-shape-memory metal includes a medical grade metal.

32. The method of claim 31, wherein the medical grade metal includes stainless steel.

33. The method of claim 18, wherein the shape-memory metal includes a medical grade metal.

34. The method of claim 33, wherein the medical grade metal includes NiTi.

35. A method of manufacturing one or more devices, the method comprising:

obtaining a base portion of a non-shape-memory metal, the non-shape-memory metal having a first base surface;

disposing one or more shape-memory metal portions along the first base surface, the one or more shape-memory metal portions having a longitudinal axis, a first portion, and a second portion axially spaced apart from the first portion along the longitudinal axis, wherein the first portion contacts the base portion and the second portion extends from the base portion;

joining a first layer of the non-shape-memory metal to the base portion using ultrasonic additive manufacturing to form a non-shape-memory portion, the first layer having a first layer surface and a second layer surface opposite from the first layer surface that is joined to the first base surface, wherein the second layer surface contacts the one or more shape-memory metal portions, wherein before joining the first layer to the base portion, disposing a radiopaque material along the first base surface, wherein the second layer surface contacts the radiopaque material when the second layer is joined to the base portion; and welding the non-shape-memory metal portion to another device that includes the non-shape-memory metal or a different non-shape-memory metal.

36. The method of claim 35, wherein joining a first layer to the base portion further includes joining one or more additional layers of the non-shape-memory metal to the previously joined layer to form the non-shape-memory portion, each of the one or more additional layers having a first layer surface and a second layer surface opposite from the first layer surface of the additional layer, the second layer surface of the additional layer being joined to the first layer surface of the previously joined layer.

37. The method of claim 35, wherein, after obtaining a base portion, the method further comprises forming one or more grooves in the first base surface, wherein the first portion of one or more of the shape-memory metal portions are disposed within the one or more grooves.

38. The method of claim 35, wherein obtaining a base portion includes joining one or more base layers of the non-shape-memory metal to each other using ultrasonic additive manufacturing, each of the one or more base layers having a first base layer surface and a second base layer surface opposite from the first base layer surface, wherein the first base layer surfaces and second base layer surfaces of adjacent base layers are joined to each other.

39. The method of claim 35, wherein obtaining a base portion includes joining one or more base layers of the non-shape-memory metal to the base portion using ultrasonic additive manufacturing to form the first base surface.

40. The method of claim 35, wherein obtaining a base portion includes machining the base portion to flatten the first base surface.

41. The method of claim 35, wherein the non-shape-memory metal includes a steel alloy, a titanium alloy, an aluminum alloy, or a copper alloy.

42. The method of claim 35, wherein the shape-memory metal includes a Cu-based alloy or a Fe-based alloy.

43. The method of claim 35, wherein the one or more shape-memory metal portions are medical instrument tips and the one or more devices manufactured by the method is a medical instrument.

44. The method of claim 35, wherein the one or more devices manufactured by the method is a medical implant.

45. The method of claim 35, wherein after joining the first layer to the base portion, the method further comprises welding the shape-memory metal portion to another device that includes the shape-memory metal or a different shape-memory metal.

46. The method of claim 35, wherein the non-shape-memory metal includes a medical grade metal.

47. The method of claim 46, wherein the medical grade metal includes stainless steel.

48. The method of claim 35, wherein the shape-memory metal includes a medical grade metal.

49. The method of claim 48, wherein the medical grade metal includes NiTi.

50. The method of claim 35, wherein, after joining the first layer to the base portion, the method further comprises machining the non-shape-memory metal portion.

51. The method of claim 50, wherein the non-shape-memory metal portion is machined using centerless grinding.

52. The method of claim 50, wherein the one or more shape-memory metal portions is two or more shape-memory metal portions, wherein the non-shape-memory metal portion is machined to form two or more separate devices, each of the devices including at least one of the two or more shape-memory metal portions.

53. A method of manufacturing one or more devices, the method comprising:
   obtaining a base portion of a non-shape-memory metal, the non-shape-memory metal having a first base surface;
   disposing one or more shape-memory metal portions along the first base surface, the one or more shape-memory metal portions having a longitudinal axis, a first portion, and a second portion axially spaced apart from the first portion along the longitudinal axis, wherein the first portion contacts the base portion and the second portion extends from the base portion;
   joining a first layer of the non-shape-memory metal to the base portion using ultrasonic additive manufacturing to form a non-shape-memory portion, the first layer having a first layer surface and a second layer surface opposite from the first layer surface that is joined to the first base surface, wherein the second layer surface contacts the one or more shape-memory metal portions;
   after joining the first layer to the base portion, welding the shape-memory metal portion to another device that includes the shape-memory metal or a different shape-memory metal; and
   welding the non-shape-memory metal portion to another device that includes the non-shape-memory metal or a different non-shape-memory metal.

54. The method of claim 53, wherein joining a first layer to the base portion further includes joining one or more additional layers of the non-shape-memory metal to the previously joined layer to form the non-shape-memory portion, each of the one or more additional layers having a first layer surface and a second layer surface opposite from the first layer surface of the additional layer, the second layer surface of the additional layer being joined to the first layer surface of the previously joined layer.

55. The method of claim 53, wherein, after obtaining a base portion, the method further comprises forming one or more grooves in the first base surface, wherein the first portion of one or more of the shape-memory metal portions are disposed within the one or more grooves.

56. The method of claim 53, wherein obtaining a base portion includes joining one or more base layers of the non-shape-memory metal to each other using ultrasonic additive manufacturing, each of the one or more base layers having a first base layer surface and a second base layer surface opposite from the first base layer surface, wherein the first base layer surfaces and second base layer surfaces of adjacent base layers are joined to each other.

57. The method of claim 53, wherein obtaining a base portion includes joining one or more base layers of the non-shape-memory metal to the base portion using ultrasonic additive manufacturing to form the first base surface.

58. The method of claim 53, wherein obtaining a base portion includes machining the base portion to flatten the first base surface.

59. The method of claim 53, wherein the non-shape-memory metal includes a steel alloy, a titanium alloy, an aluminum alloy, or a copper alloy.

60. The method of claim 53, wherein the shape-memory metal includes a Cu-based alloy or a Fe-based alloy.

61. The method of claim 53, wherein the one or more shape-memory metal portions are medical instrument tips and the one or more devices manufactured by the method is a medical instrument.

62. The method of claim 53, wherein the one or more devices manufactured by the method is a medical implant.

63. The method of claim 53, wherein before joining the first layer to the base portion, the method further comprises disposing a radiopaque material along the first base surface, wherein the second layer surface contacts the radiopaque material when the second layer is joined to the base portion.

64. The method of claim 53, wherein the non-shape-memory metal includes a medical grade metal.

65. The method of claim 64, wherein the medical grade metal includes stainless steel.

66. The method of claim 53, wherein the shape-memory metal includes a medical grade metal.

67. The method of claim 66, wherein the medical grade metal includes NiTi.

68. The method of claim 53, wherein, after joining the first layer to the base portion, the method further comprises machining the non-shape-memory metal portion.

69. The method of claim 68, wherein the non-shape-memory metal portion is machined using centerless grinding.

70. The method of claim 68, wherein the one or more shape-memory metal portions is two or more shape-memory metal portions, wherein the non-shape-memory metal portion is machined to form two or more separate devices, each of the devices including at least one of the two or more shape-memory metal portions.

* * * * *